United States Patent [19]

Spencer

[11] 4,208,129
[45] Jun. 17, 1980

[54] SENSITIVE LASER SPECTROSCOPY MEASUREMENT SYSTEM

[75] Inventor: Donald J. Spencer, Torrance, Calif.

[73] Assignee: The United States of America as represented by the Secretary of the Air Force, Washington, D.C.

[21] Appl. No.: 921,137

[22] Filed: Jun. 30, 1978

[51] Int. Cl.$^2$ ............................ G01J 3/46; G01J 3/42
[52] U.S. Cl. .................................. 356/425; 356/325; 356/435
[58] Field of Search ............... 356/323, 325, 425, 435, 356/437; 250/575

[56] References Cited

U.S. PATENT DOCUMENTS

| | | | |
|---|---|---|---|
| 2,858,727 | 11/1958 | Stamm et al. | 356/435 |
| 3,443,089 | 5/1969 | Sundstrom | 356/323 |
| 3,583,813 | 6/1971 | Shibata et al. | 356/325 |
| 3,782,828 | 1/1974 | Alfano et al. | 356/323 |
| 3,810,696 | 5/1974 | Hutchins, Jr. | 356/435 |
| 3,871,771 | 3/1975 | Scott | 356/114 |
| 3,966,328 | 6/1976 | Wirlund | 356/138 |

OTHER PUBLICATIONS

"Fluorine Pressure Change Monitor for a Reacting System"; Schard et al; Rev. Sci. Inst.; vol. 43 #11; Nov. 72, p. 1717-1718.
"Initial Performance of a CW Chemical Laser"; Spencer et al; Opto-Electronice; vol. 2, pp. 155-160, 1970.
Numerical Study of a Diffusion Type Chemical Laser"; King et al; AIAA Paper No. 72-146, presented at 10th Aerospace Sciences Meeting, San Diego, Ca. 17-19 Jan. 1972.
"Boundary Layer Effects in Chemical Laser Nozzle Inlet"; Mirels et al; The Aerospace Corp. Report Samso-TR-77-211 11/8/77.
"CL X1 Nozzle F$_2$ Absorption Experiment" Samso--TR-77-107, 6/15/77; published 7/6/77.

*Primary Examiner*—Vincent P. McGraw
*Attorney, Agent, or Firm*—Joseph E. Rusz; Jacob N. Erlich

[57] ABSTRACT

A sensitive laser spectroscopy measurement system having a laser radiation source and a dual beam and detection scheme that allows for the measurement of small intensity differences between a probe beam and a reference beam resulting from the absorption, gain or scattering of the probe beam by a medium placed in its optical path. The system attains measurement sensitivities of less than $10^{-4}$ when the laser radiation source for the probe and reference beams is modulatable. Further included within the system is a prism placed in the optical path of the laser beam before the beam splits into the probe and reference beams and a detector for each beam. The detectors are electrically connected to a sensitivity differential amplifier and an oscilloscope for displaying the intensities of the beams.

10 Claims, 1 Drawing Figure

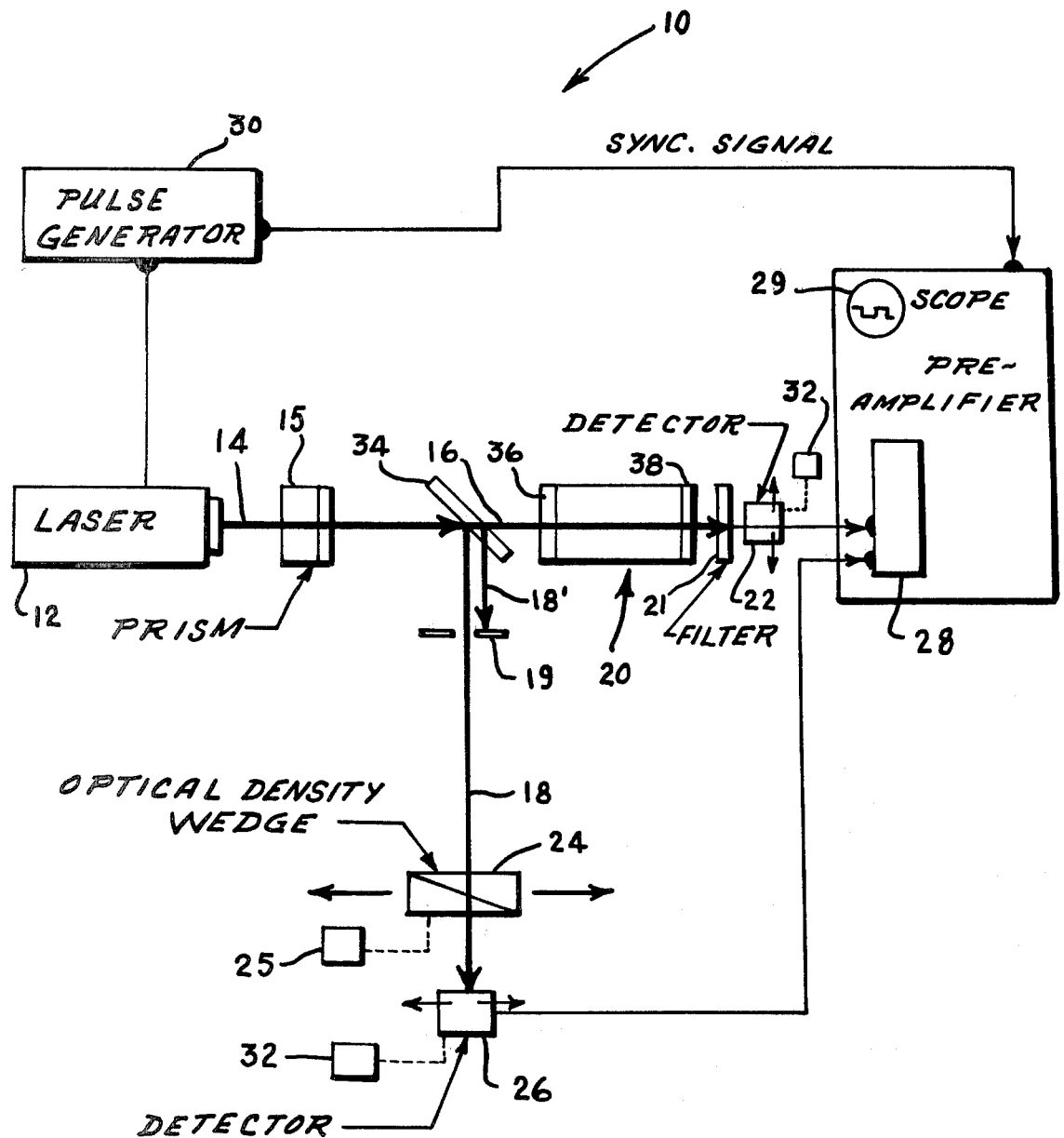

4,208,129

SENSITIVE LASER SPECTROSCOPY MEASUREMENT SYSTEM

STATEMENT OF GOVERNMENT INTEREST

The invention described herein may be manufactured and used by or for the Government for governmental purposes without the payment of any royalty thereon.

BACKGROUND OF THE INVENTION

This invention relates generally to spectroscopy measurement techniques, and, more particularly to a sensitive laser spectroscopy measurement system which is capable of attaining measurement sensitivities of less than $10^{-4}$ at the UV, visible and near IR wavelength.

A measurement problem frequently encountered in the laboratory involves the determination of a small signal change from an illuminated detector resulting from a minute change in absorption, gain or scattering of the light in a measurement region which lies between the light source and the radiation sensitive detector. For example, in the analysis of HF/DF chemical lasers the uncertainties in the F-atom concentration in the cavity flow region have hampered chemical efficiency calculation and plagued analytical attempts to model this type of laser. F-atom uncertainties in the cavity region arise both as a result of uncertainties in the F-atom concentration in the plenum and uncertainties introduced by wall recombination of F-atoms in the expansion nozzle. This situation exists for both arc-heated and combustion-heated chemical lasers.

Heretofore various techniques have been utilized to enhance sensitivities of this type of measurement. One such technique by Suchard is Bergerson and presented in an article entitled "Flourine Pressure Change Monitor For a Reacting System", The Review of Scientific Instruments, Volume 43, No. 11, November 1972, pp 1717. This technique utilizes a dual beam, a mechanical chopper and a single photomultiplier detector with an achieved intensity sensitivity measurement capability of $2.5 \times 10^{-3}$. In addition, commercial units called ratio meters that measure the ratio of probe to reference beam intensities have been developed by both the ITHACO (model 3512) and P.A.R. (model 188) which utilize laser beam optical sources, mechanical choppers with different frequencies for the reference and probe beams, two phase sensitive lock-in amplifiers and a photomultiplier detector for signal measurement. The sensitivities of these instruments are of the order of $5 \times 10^{-3}$.

Consequently, when a need emerges for the measurement of, for example, low $F_2$ concentration in HF/DF chemical laser flow which requires a sensitivity in the order of less than $10^{-4}$ the techniques of the type listed above fall well short of the required sensitivities.

SUMMARY OF THE INVENTION

The instant invention overcomes the problems encountered in the past by providing a sensitive laser spectroscopy measurement system which is capable of increased sensitivity of 1 to 2 orders of magnitude over the devices used in the past. This is accomplished from the concomitant use of 100 percent internal laser modulation, 100 percent plane beam polarization, silicon photovoltaic detection and detector positioning capability transverse to the beam. In addition, reduced complexity in implementation of sensitive spectroscopy is achieved, as well as scope display of the differential signal resulting therefrom.

The sensitive laser spectroscopy measurement system of this invention is made up of a radiation source which provides a beam of radiant energy utilized in the spectroscopy measurement. This radiation source must provide an output power of at least 1 mW and must be internally modulatable with 100 percent modulation depth. Initially the beam emanating from the radiation source passes through a prism placed in the optical path of the laser beam before the beam is split into the probe and reference beam. After the splitting of the beam, the reference beam passes through a linear optical density wedge of limited opacity range and then onto a photovoltaic detector. The probe beam passes through the absorption measurement region which is bounded by a pair of suitable high quality optical flats which are employed as the absorption region windows. After passing through the absorption measurement region the probe beam then enters a photo voltaic detector. The pair of photovoltaic detectors are electrically connected to a conventional sensitive differential amplifier and a conventional oscilloscope for displaying the differential intensity signals.

Spectroscopy measurements with the system of the instant invention is made in the following manner. The original beam intensity, $I_o$, is determined on the oscilloscope trace as the peak-to-zero signal difference of the modulated probe-beam detector for no absorption (gain) in the measurement region. The reference and probe beam detector signals are brought into coincidence within the required sensitivity of less than $10^{-4}$ by viewing the different signals at decreasing amplifier gain levels while reducing the detector light differential through the positioning of the optical density wedge. The introduction of absorption (gain) into the measurement region results in measurement of the differential signal, $\Delta I$, (the change in probe beam intensity relative to reference beam intensity).

It is therefore an object of this invention to provide a sensitive laser spectroscopy measurement system which is capable of increased sensitivity by 1 to 2 orders of magnitude over devices of the past.

It is another object of this invention to provide a sensitive laser spectroscopy measurement system which is simplistic in design as a result of the use of internal laser modulation and separate detection of probe and reference beams.

It is still another object of this invention to provide a sensitive laser spectroscopy measurement system which provides a visual real time scope display of differential signals.

It is a further object of this invention to provide a sensitive laser spectroscopy measurement system which is economical to produce and which utilizes conventional, currently available components that lend themselves to standard mass producing manufacturing techniques.

For a better understanding of the present invention, together with other and further objects thereof, reference is made to the following description taken in conjunction with the accompanying drawing and its scope will be pointed out in the appended claims.

DETAILED DESCRIPTION OF THE DRAWINGS

The only FIGURE of the drawing is a schematic diagram of the sensitive laser spectroscopy measurement system of this invention.

DETAILED DESCRIPTION OF THE PREFERRED EMBODIMENT

Reference is now made to the only FIGURE of the drawing which shows in schematic fashion the sensitive laser spectroscopy measurement system 10 of this invention. System 10 permits the differential measurement of small intensity changes during, for example, a spectroscopy measurement procedure as a result of the insertion within the system of an absorbing medium such as $F_2$. The measurement sensitivities accomplished by system 10 of this invention are less than $10^{-4}$ and in some cases as sensitive as $2 \times 10^{-5}$.

As clearly illustrated in the only FIGURE of the drawing the laser spectroscopy measurement system 10 is made up of a laser 12 which produces laser beam 14. Laser beam 14 passes through a prism 15 before being split into a pair of beams, probe beam 16 and reference beam 18. Probe beam 16 passes through an absorption measurement region 20 a filter 21 before entering photovoltaic detector 22. Reference beam 18 passes through an optical density wedge 24 before entering photovoltaic detector 26. A more detailed explanation of these optical paths and the elements located therein will be set forth in detailed hereinbelow. Detectors 22 and 26 are electrically connected to a conventional amplifier 28 and oscilloscope 29.

Referring once again to laser 12, it is essential in the laser spectroscopy measurement system 10 of this invention that laser 12 have an output level greater than 1 mW and a wavelength from approximately 0.19 to 1.15 μm. These constraints are imposed upon laser 12 by the sensitivity of detectors 22 and 26. In addition, laser 12 must be internally modulatable with 100 percent modulation depth.

Two internal modulation schemes may be utilized with the instant invention. For example, an acousto-optic intracavity modulation system may be used wherein a conventional pulse generator 30 such as an Interstate Electronics Model P25 is electrically connected to a modulatable laser such as an Liconix Model 301M Laser as well as being electrically connected to oscilloscope 28 providing a sync. signal therefore. It is also possible to utilize a conventional plasma modulation system in this invention in which pulse generator 30 may be omitted. These methods of modulation produce undistorted beams colinear with the optic axis during the modulation process, minimizing or eliminating the switching transients caused by a scanning of the probe and reference beams 16 and 18, respectively, over different inhomogeneous optical surfaces during chopping such as in mechanical systems.

Intensity differences in the two light paths 16 and 18 of system 10 may develop due to polarization effects. Since reflectivity and transmissivity of the optical components in the optical paths are functions of the incident beams polarization, independent intensity changes in the two polarization components (vertical and horizontal) of an unpolarized laser beam may produce uncompensated beam intensity changes. Hence, a conventional sapphire prism 15 is placed in the optical path of beam 14 before beam 14 splits into probe and reference beams 16 and 18, respectively, thereby eliminating the horizontal component and providing substantially totally (100 percent) vertically polarized beam.

Beam 14 is split into probe and reference beams 16 and 18 by preferably a thick optical dielectric flat or an optical wedge utilized as a beam splitter 34. Such a component allows for the easy elimination of one of the reflected beams 18' by a conventional optical stop 19 placed in its path to avoid noise generation in the reference beam detector 26 due to interference. The angle of orientation of the beam splitter 34 relative to the incident beam 14 is nominally 45°, but may be varied within limits to help achieve a closer balance in the probe and reference beam intensities at detectors 22 and 26, respectively. The use of an uncoated dielectric flat is used for the situation in which probe beam detector 22 requires use of a narrow band optical transmisstion filter 21 with reduced in-band transmission, which reduces the transmitted or probe beam 16 of beam splitter 34 and brings it into closer balance with the reflected or reference beam 18. If no optical filter 21 is required an approximately 45 percent T approximately 55% R dielectric coated mirror may be utilized in place thereof.

As pointed out hereinabove and clearly illustrated in the drawing reference beam 18 also passes through a suitable linear optical density wedge 24 of limited opacity range (e.g., quartz, 0–0.3). Translation of optical density wedge 24 by any suitable moving means such as motor 25 transverse to the optical path of beam 18 allows refined intensity reduction of beam 18 to bring the intensity of the two beams 16 and 18 measured at detectors 22 and 26, respectively, into the condition of zero differential signal.

As set forth hereinabove probe beam 16 passes through an absorption measurement region or absorption cell 20 formed between a pair of windows 36 and 38 in the form of any suitable high quality optical flats (e.g., $CaF_2$, quartz, etc.).

Other restrictions placed on the system 10 of this invention are that beam 14 must be free of any limiting apertures in the optical path between laser 12 and detectors 22 and 26 and the optical path length between laser 12 and detectors 22 and 26, respectively, should be approximately the same to insure nearly equal spot sizes.

Detectors 22 and 26 are conventional photovoltaic detectors such as EG and G Model UV 44B silicon photovoltaic detectors. Detectors 22 and 26 are electrically connected to a differential amplifier 28 and an oscilloscope 29. The differential amplifier may be of the type produced by Tektronix as Model No. 1A7A of 10 μv sensitivity and the oscilloscope as Model No. 545. The load resistors in each were 1000Ω. This value load resistor maintained photovoltaic operation in the linear region of the characteristic curve. The detectors radiation power sensitivity are nominally a constant value (within approximately 2%) over the entire detector surface. In addition it is necessary to provide detectors 22 and 26 with translation capability in the two directions transverse to beams 16 and 18, respectively, by means of any suitable moving means such as motors 32 to allow tuning of the beams to the peak sensitivity spots. This procedure is essential to achieving measurement stability since beam jitter on the side of the peak would result in differentially uncompensated signals being generated. However, with both detectors peaked, signal changes due to beam jitter can be minimized to an acceptable level.

In operation, initially absorption measurement region 20 is darkened for testing, and detectors 22 and 26 are tuned for optimum gain by translation transverse beams 16 and 18, respectively. The low pass filter of differential amplifier 28 eliminates high-frequency noise above 100 Hz. The measurement of the intensity, $I_o$, of probe beam 16 is read directly on scope 29 with the absorption measurement region 20 empty. The intensity of reference beam 18 is then made equal to the intensity of probe beam 16 to at least one part in $10^4$ by means of the optical density wedge 24. With the addition of a gas to be measured such as $F_2$ within the absorption measurement region 20, the measured intensity difference $\Delta I$ resulting from $F_2$ absorption can be read directly on the scope 29 at a high sensitivity as the difference between the modulated-on and modulated-off beam traces. The $F_2$ density for small concentration will determine directly from the equation $$p_{F_2} \text{ (mol/l)} = \frac{1}{8.70 \, L \text{ (cm)}} \frac{\Delta I}{I_o}$$

where the absorbtion coefficient is 8.70, L is the absorption path length, and $p_{F_2}$ is the molecular fluorine molar density, $\Delta I$ is the difference between the probe beam 16 intensity and the reference beam 18 intensity and $I_o$ is the original probe beam 16 intensity with no $F_2$ in region 20.

Since the sensitivity of the laser spectroscopy measurement system 10 of the invention is well within $10^{-4}$ the instant invention is capable of increased spectroscopy measurements and experimentation in the UV, visible and near IR wavelengths.

Although this invention has been described with reference to a particular embodiment, it will be understood that this invention is also capable of further and other embodiments within the spirit and scope of the appended claims.

I claim:

1. A sensitive laser spectroscopy measurement system comprising means for producing a beam of radiant energy, means operably connected to said radiant energy producing means for internally controlling the modulation of the beam of radiant energy produced thereby, means in optical alignment with said beam of radiant energy for producing a substantially totally vertically polarized beam of radiant energy, means in optical alignment with said beam of radiant energy for splitting said beam into a probe beam and a reference beam of radiant energy, said probe and reference beams of radiant energy each following different optical paths, the length of each of said optical paths being substantially the same, means in optical alignment with said probe beam of radiant energy for encompassing a medium on which said spectroscopy measurement is to be performed, photovoltaic detection means located adjacent said medium encompassing means and in optical alignment with said probe beam for measuring the intensity of said probe beam, means in optical alignment with said reference beam for altering the intensity of said reference beam, photovoltaic detection means located adjacent said intensity altering means and in optical alignment with said reference beam for measuring the intensity of said reference beam, means attached to both of said photovoltaic detection means to provide two-dimensional transverse movement of both of said photovoltaic detection means relative to both said probe and reference beams for fine tuning to sensitivity peaks of said photovoltaic detection means, and means operably connected to both of said photovoltaic detection means for displaying said intensities of said probe beam and said reference beam whereby the intensity difference between said probe beam and said reference beam can be observed with extremely high sensitivity on said display means.

2. A sensitive laser spectroscopy measurement system as defined in claim 1 wherein said intensity altering means is in the form of a linear optical density wedge.

3. A sensitive laser spectroscopy measurement system as defined in claim 2 wherein said vertically polarizing producing means is in the form of a sapphire prism.

4. A sensitive laser spectroscopy measurement system as defined in claim 3 wherein both of said intensity measuring means are in the form of a silicon photovoltaic detector.

5. A sensitive laser spectroscopy measurement system as defined in claim 4 wherein said medium encompassing means is in the form of a cell having a pair of high quality optical windows at each end thereof.

6. A sensitive laser spectroscopy measurement system as defined in claim 5 further comprising a filter in optical alignment with said probe beam and interposed between said medium encompassing means and said probe beam detector.

7. A sensitive laser spectroscopy measurement system as defined in claim 5 wherein said beam splitting means is in the form of a thick optical dielectric flat.

8. A sensitive laser spectroscopy measurement system as defined in claim 7 wherein said display means is in the form of an oscilloscope.

9. A sensitive laser spectroscopy measurement system as defined in claim 1 wherein said means for modulating said beam of radiant energy is in the form of a pulse generator, said pulse generator being operably connected between said means for producing a beam of radiant energy and said display means.

10. A sensitive laser spectroscopy measurement system as defined in claim 1 wherein said radiant energy producing means is in the form of a modulatable laser.

* * * * *